United States Patent
Momma et al.

(10) Patent No.: US 9,737,077 B2
(45) Date of Patent: Aug. 22, 2017

(54) METHOD FOR CONTROLLING SEXUALITY OF HOP

(75) Inventors: Takayuki Momma, Nakano-ku (JP); Naoyuki Umemoto, Nakano-ku (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 424 days.

(21) Appl. No.: 14/239,718

(22) PCT Filed: Aug. 10, 2012

(86) PCT No.: PCT/JP2012/070873
§ 371 (c)(1),
(2), (4) Date: Feb. 19, 2014

(87) PCT Pub. No.: WO2013/027659
PCT Pub. Date: Feb. 28, 2013

(65) Prior Publication Data
US 2014/0196164 A1    Jul. 10, 2014

(30) Foreign Application Priority Data
Aug. 19, 2011  (JP) ................................ 2011-179873

(51) Int. Cl.
| | |
|---|---|
| *A01N 59/00* | (2006.01) |
| *A01N 59/16* | (2006.01) |
| *A01H 3/04* | (2006.01) |
| *A01H 5/02* | (2006.01) |
| *A01N 37/44* | (2006.01) |
| *A01N 59/06* | (2006.01) |
| *C12Q 1/68* | (2006.01) |
| *A01N 27/00* | (2006.01) |
| *A01N 37/36* | (2006.01) |

(52) U.S. Cl.
CPC .............. *A01N 59/16* (2013.01); *A01H 3/04* (2013.01); *A01H 5/02* (2013.01); *A01N 27/00* (2013.01); *A01N 37/36* (2013.01); *A01N 37/44* (2013.01); *A01N 59/00* (2013.01); *A01N 59/06* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| PP8,812 P | * | 6/1994 | Probasco ................. | A01H 5/00 |
| 7,387,205 | B1 * | 6/2008 | Wilson ............... | B65D 33/2591 |
| | | | | 206/204 |
| 2013/0062242 | A1 * | 3/2013 | De Heij ................ | B65B 25/041 |
| | | | | 206/524.6 |

OTHER PUBLICATIONS

Weston, Nature (1960) 188: 81-82.*
Ram and Sett, Theor. Appl. Genet. 1982, vol. 62, pp. 369-375.*
Ram, Research Gate, Jan. 1982, Abstract.*
USDA Natural Resources Conservation Service, Classification Report Family Cannabaceae, 2005.*
Ecochem Web Page, 2005, Foliar Fertilizer Benefits.*
Jernej Jakse, et al., "Microsatellite variability among wild and cultivated hops (Humulus lupulus L.)," Genome, 2004, pp. 889-899, vol. 47.
John A. Henning, et al, "Potential Heterotic Crosses in Hops as Estimated by AFLP-Based Genetic Diversity and Coefficient of Coancestry," Journal of the American Society of Brewing Chemists, 2004, pp. 63-70, vol. 62, No. 2.
J.H. Henning, et al., "Predicting Offspring Performance in Hop (Humulus lupulus L.) Using AFLP Markers", Journal of the American Society of Brewing Chemists, 2010, pp. 125-131, vol. 68, No. 3.
E.W. Weston, "Changes in Sex in the Hop caused by Plant Growth Substances", Nature, Oct. 1, 1960, pp. 81-82, vol. 188, No. 4744.
Sachihiro Matsunaga, "Sex Determination of Higher Plants", Protein Nucleic Acid Enzyme, 2000, pp. 1704-1712, vol. 45, No. 10.
H.L. Shephard, et al., "Sexual development and sex chromosomes in hop", New Phytol., 2000, pp. 397-411, vol. 148.
Atewell, B., et al., "Plant in Action", Turbull Macmillan Education Australia, 1999, pp. 244-247.
Ivan F. Acosta, et al, "tasselseed1 Is a Lipoxygenase Affecting Jasmonic Acid Signaling in Sex Determination of Maize", Science, Jan. 9, 2009, pp. 262-265, vol. 323.
Dong-Hui Wang, et al., "Ethylene perception is involved in female cucumber flower development," The Plant Journal, 2010, pp. 862-872, vol. 61.
Mohammad Ali, et al., "Techniques for propagation and breeding of kakrol (Momordica dioica Roxb.)", Scientia Horticulturae, 1991, pp. 335-343, vol. 47.
H.Y. Mohan Ram, et al., "Induction of Fertile Male Flowers in Genetically Female Cannabis sativa Plants by Silver Nitrate and Silver Thiosulphate Anionic Complex", TAG, 1982, pp. 369-375, vol. 62.
International Search Report for PCT/JP2012/070873, dated Sep. 25, 2012.

* cited by examiner

*Primary Examiner* — Eileen O Hara
(74) *Attorney, Agent, or Firm* — Sughrue Mion, PLLC

(57) ABSTRACT

This invention relates to: a method for controlling the sexuality of hop, comprising applying a chemical to a hop female plant once or more and forming a fertile male flower capable of forming pollen on the female plant, wherein the chemical reduces a reaction with endogenous ethylene in the female plant; an embryo or seed, hop plant, and cone, capable of being obtained through the method; a method of screening for a hop plant; and a method of producing a hop plant variety.

5 Claims, 7 Drawing Sheets
(5 of 7 Drawing Sheet(s) Filed in Color)

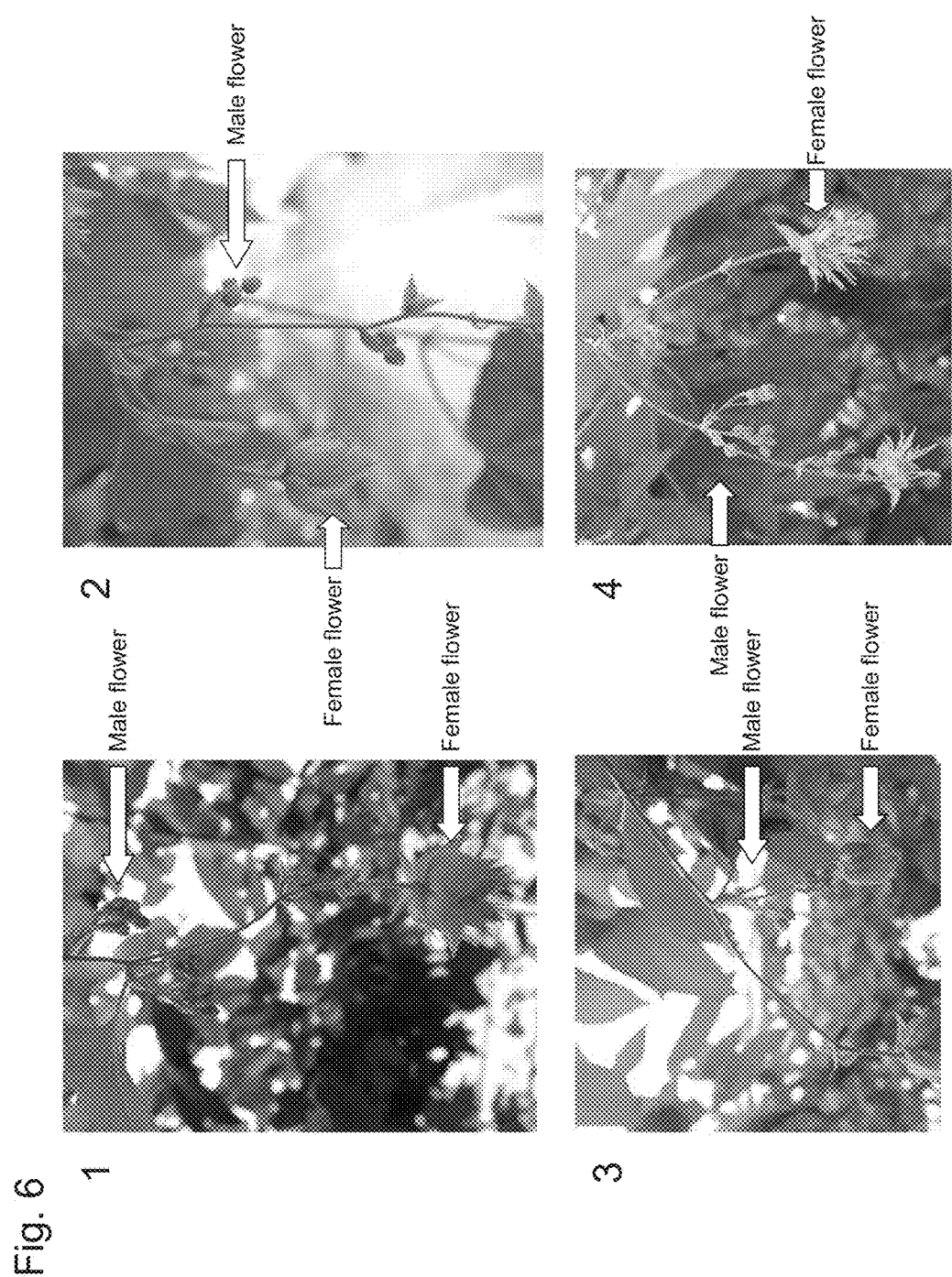

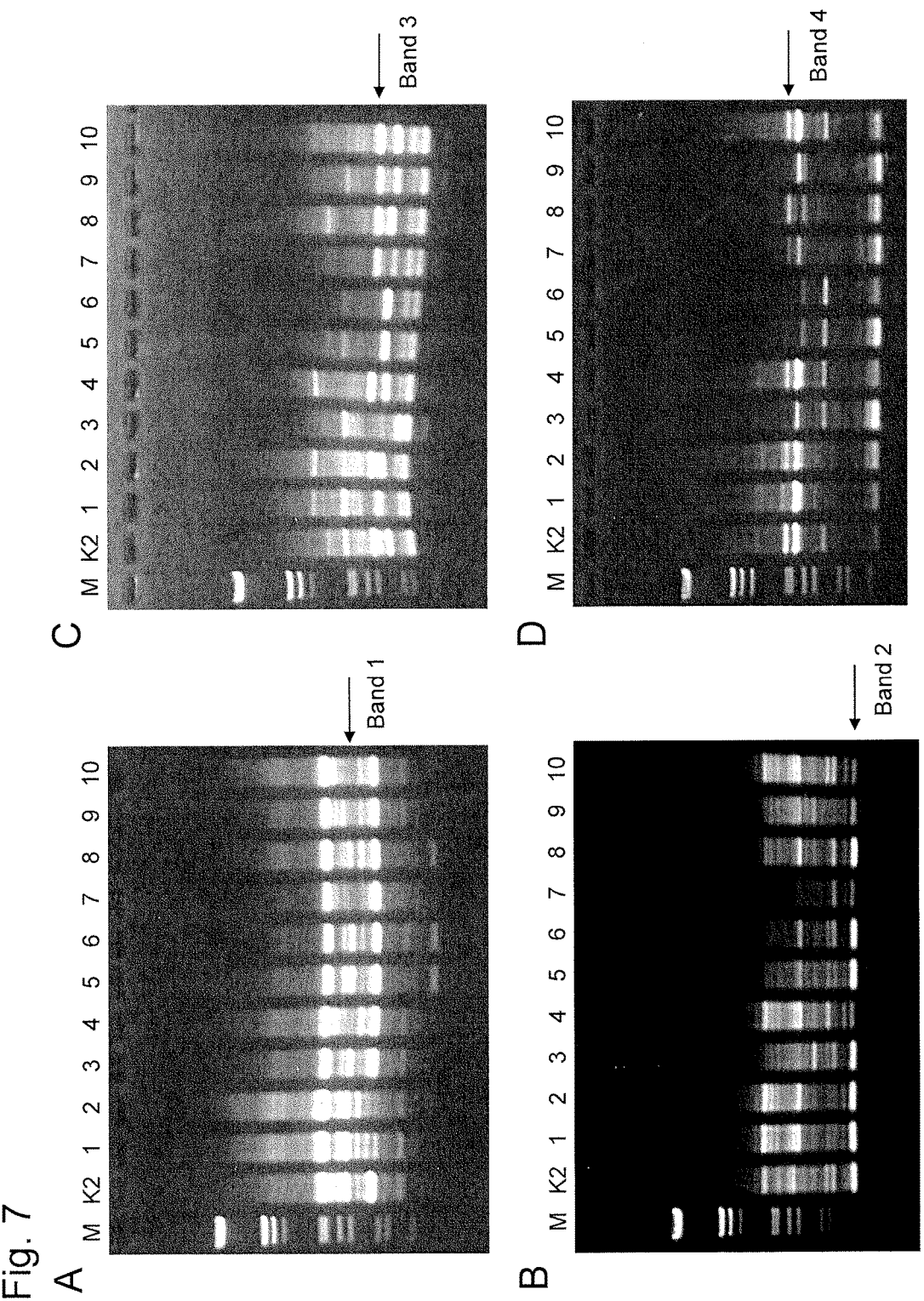

METHOD FOR CONTROLLING SEXUALITY OF HOP

CROSS REFERENCE TO RELATED APPLICATIONS

This application is a National Stage of International Application No. PCT/JP2012/070873, filed Aug. 10, 2012, claiming priority based on Japanese Patent Application No. 2011-179873, filed Aug. 19, 2011, the contents of all of which are incorporated herein by reference in their entirety.

TECHNICAL FIELD

The present invention relates to a method for forming a male flower on a hop female plant and a use of the method.

BACKGROUND

A cone, which is a female flower formed on a female plant of hop (*Humulus lupulus*) that is a dioecious plant, is an important raw material used for brewing beer. The cone of hop contains bitter acid, terpenoid, polyphenol, and the like, and is deeply associated with the flavor of beers. Since only the cone is utilized as the raw material, only the female plant is used for cone production. Also, as an unpollinated cone is a good quality raw material, male plans are not only unneeded at cone-producing districts but male plants become a cause of poor quality and is hence not cultivated intentionally.

Meanwhile, the male plant is utilized for breeding. The breeding of hop is practiced by cultivating, propagating and evaluating plant individuals derived from seeds obtained by crossbreeding the pollen of a male flower formed on a male plant with the female flower of a female plant, and screening for a desirable individual. The utilized male plant cannot form a female flower thereon, and thus the cone as the raw material cannot be evaluated. Accordingly, a male plant is utilized on the presumption of genetic abilities thereof based on cone evaluation of sister individuals thereof or cone evaluation of offsprings produced with other female plants. However, hop is a vegetative propagation crop and has high genetic heterozygosis which makes it difficult to presume such ability, and thus an efficient breeding strategy on the cone evaluation is in demand. Further, the male plant is required to be maintained only to be utilized for the breeding.

To solve these problems and practice the breeding efficiently, a strategy is conceived that the male plant is not utilized, that is, a male flower is intentionally induced to develop on a female plant to crossbreed female plants with each other. Up to date, it is documented that a male flower was formed on a hop female plant by spraying 500 ppm α (2-chlorophenylthio)propionic acid, sodium salt, wherein an involvement with auxin, a plant hormone, was examined (Non Patent Literature 1). However, this document merely describes that the male flower was formed and it is not clear whether the pollen formation, fertility, and the like, were achieved therein. Regarding the formation of an male flower on a hop female plant, the use of such an auxin-related substance was the only single report documented half a century ago, and α (2-chlorophenylthio)propionic acid has not been utilized for the breeding of hop ever since.

In the dioecious plants whose sexuality is genetically determined, the XY type is the most common but the ZW type is also known, and the sex determination is roughly divided into the species in which the male sex determination factor is presumably present in the Y chromosome even in the XY type and the species in which the sex is determined by the ratio of the X chromosome to the autosome (Non Patent Literature 2), thus suggesting a diverse genetic background in the sex determination. It is reported that the sexuality of hop is determined by the ratio of the X chromosome to the autosome (Non Patent Literature 3). Non Patent Literature 4 describes that morphic sex chromosomes were found in asparagus and hop and thus the sex is determined by the presence of sex gene on the sex chromosomes. On the other hand, this literature indicates, in reference with the following examples, that plant hormones are involved with the sex determination in many plants having no such property. Auxin and ethylene promote the feminization in the Cucurbitaceae (cucumber), pineapple, papaya and date, and gibberellin promotes the masculinization in the Cucurbitaceae, mulberry (mulberry belonging to the Moraceae) and oil palm, and cytokinin induces a hermaphrodite flower in the male grape. Further, the literature refers to that the actions rendered by these plant hormones include many exceptions. For example, auxin promotes the formation of *Pseudotsuga* male buds, and ethylene promotes the masculinization of Chinese chestnut, and female flowers of locust beans gum and date palm contain a higher level of gibberellin than male flowers thereof and the addition of gibberellin promotes the feminization in corn and Chinese chestnut, or the like. Regarding such a confusing ununified incomprehensible situation, Non Patent Literature 4 points out that such a situation might be caused by a mismatch between the physiological plant hormone level and the chemical concentration externally administered. Also, this literature describes that, even in the Cucurbitaceae which has been well studied, the part of a plant, environmental factors (i.e., light intensity, nutrient conditions, temperature, day length conditions) influence the changes in sex. As described above, Non Patent Literature 4 suggests that the sex determination of hop is not associated with plant hormones but depends on morphic sex chromosomes. Further, the literature includes examples illustrating the conflicting effects that different plant hormones promote the feminization or the masculinization depending on the plant species or concentrations in a case of the plant with which plant hormones are associated.

Plant hormones are, in many cases, involved with the sex determination and sexual differentiation of plants which is documented in auxin, gibberellin, cytokinin, ethylene, and the like, and there is an opinion that there is no plant hormone which works commonly on higher plants (Non Patent Literature 2). Furthermore, in recent years, it is suggested that in corn, which is a dioecious flower, the pistil is degenerated due to jasmonic acid, which is one of plant hormones, and transformed to the male flower (Non Patent Literature 5). Thus, in the sex determinations in the plants, mechanisms differ due to the various plant hormones and so it is considered that each has independently evolved. The study on the sex conversion in plant species associated with ethylene has been progressed using the Cucurbitaceae crops. The Cucurbitaceae crops are dioecious plants, and female flowers and male flowers are respectively formed on a genetically identical single plant by physiological factors. In the Cucurbitaceae crops, a case of inducing female flowers by ethylene treatment is known, and in cucumber it is suggested that the stamen development is inhibited by ethylene and an female flower is formed thereon (Non Patent Literature 6). Further, it is reported that a hermaphrodite flower is formed when a female plant of *Momordica dioica* plant belonging to the Cucurbitaceae, a dioecious plant, is treated with silver nitrate, which is an ethylene inhibitor (Non Patent Literature 7). Furthermore, it is reported that in *Cannabis sativa* belonging to the *Cannabis*, a dioecious plant, when silver nitrate or STS (silver thiosulphate anionic complex), an ethylene inhibitor, is applied to a growing shoot tip, which becomes black, an intersex flower, an incomplete male flower with few stamens or a complete male flower, together with female flowers, were formed on the main branch and lateral branches which grow thereafter (Non Patent Literature 8).

PRIOR ART LITERATURE

Non Patent Literature

Non Patent Literature 1: Weston, E. W. Nature (1960) 188:81-82
Non Patent Literature 2: Matsunaga, Sachihiro, Protein, Nucleic acid, Enzyme (2000) 45:1704-1712
Non Patent Literature 3: Shephard, H. L et al. New Phytol. (2000) 148:397-411
Non Patent Literature 4: Plant in action (1999), edited by Atewell, B. et al, Turnbull Macmillan Education Australia, p. 244-p. 247
Non Patent Literature 5: Acosta, I. F. et al Science (2009) 323:262-265
Non Patent Literature 6: Wang, D-H. et al. Plant J. (2010) 61:862-872
Non Patent Literature 7: Ali, M et al. Scientia Hortic. (1991) 47: 335-343
Non Patent Literature 8: Mohan, H. Y. and Sett, R. Theor. Appl. Genet. (1982) 62:369-375

SUMMARY OF INVENTION

The hop belonging to the genus *Humulus* requires several years before obtaining flowers sufficiently, and it takes 10-20 years for productivity tests of the cone which is an unpollinated female flower. It is said that it takes 20 to 30 years before 1 variety is selectively bred. When crossbreeding female plants with each other, which are utilized for the production and whose cone quality and productivity are verified, becomes possible, the plant breeding program would become simpler. The progenies from the female-male crossbreeding include unnecessary male plants, however, the progenies from female plants crossbred with each other are theoretically all female plants. Further, the maintenance and evaluation of male plants for the breeding will be completely unneeded. In these respects, the breeding efficiency is also improved. Currently, the construction of hop genetic map has been attempted in different places. When the crossbreeding between female plants becomes possible, the parents used in the crossbreeding and all individuals of the next generation and the more future generations obtained from the parents can be evaluated for their cone quality and productivity, whereby improved construction efficiency of the genetic map (linkage map), improved precision, or the like, is expected. Thus, where the formation of male flowers on a female plant becomes possible, inestimable economic effects such as cost, time, and the like, in the genetic analysis and breeding are expected. Despite such a technology much anticipated, no technology in which a male flower is induced from a female plant to make it possible to practice the crossbreeding between female plants has been established in hop.

An object of the present invention is to provide a method for physiologically controlling the sexuality of hop so as to enable the crossbreeding between female plants without utilizing male plants in order to contribute efficient breeding of dioecious hops, more specifically, a method for making a male flower intentionally formed on a female plant.

To solve the above problems, the present inventors studied different chemicals and treatment methods thereof, and have now found that a male flower can be formed on a hop female plant by reducing the reaction with endogenous ethylene, a plant hormone. The present inventors further examined the properties of pollen and seed production abilities of the bloomed male flowers. Through such studies, the present invention was accomplished. The reaction with endogenous ethylene can be reduced by applying an ethylene biosynthesis inhibitor, an ethylene action inhibitor, an ethylene adsorbent, or a combination thereof.

The present invention comprises the following method for physiologically controlling the sexuality of hop, as well as the following seed, plant and cone obtained by using the method for physiologically controlling the sexuality of hop.

(1) A method for controlling the sexuality of hop, comprising applying a chemical to a hop female plant once or more and thereby forming a fertile male flower capable of producing pollen on the female plant, wherein the chemical reduces a reaction with endogenous ethylene in the female plant.

(2) The method of (1) above, wherein the chemical is an ethylene biosynthesis inhibitor, an ethylene action inhibitor, an ethylene adsorbent, or a combination thereof (3) The method of (2) above, wherein the ethylene biosynthesis inhibitor is selected from the group consisting of aminooxyacetic acid, 2-aminoisobutylic acid, amino ethoxy vinyl glycine (AVG), cobalt chloride, and rhizobitoxine.

(4) The method of (2) above, wherein the ethylene action inhibitor is selected from the group consisting of silver thiosulfate complex (STS), 1-methylcyclopropene, and silver nitrate.

(5) The method of (2) above, wherein the ethylene adsorbent is activated carbon or zeolite.

(6) The method of any of (1)-(5) above, comprising applying the chemical to a hop female plant before flower bud differentiation.

(7) The method of any of (1)-(6) above, wherein the chemical application is a foliar application or foliar spray.

(8) An embryo or a seed, which is capable of being obtained by: producing a female plant with a male flower formed thereon using the method of any of (1)-(7) above; and crossbreeding pollen of the female plant and a female flower of the female plant or a female flower of another female plant.

(9) A hop plant capable of being produced from the embryo or the seed of (8) above.

(10) A cone from the hop plant of (9) above.

(11) A method of screening for a hop plant, comprising breeding hop plants from different embryos or seeds of (8) above, determining, as a genetic marker, a DNA polymorphism linking to a trait characteristic of each hop plant, making a genetic linkage map between the genetic marker and the trait, and screening for a hop plant of interest from the hop plants using the genetic linkage map.

(12) A method for producing a hop plant variety, comprising a step of forming a fertile male flower capable of producing pollen on a hop female plant.

(13) The method according to (12) above, wherein forming the male flower is conducted by applying a chemical to a hop female plant once or more, wherein the chemical reduces a reaction with endogenous ethylene in the hop female plant.

(14) The method of (13) above, comprising applying the chemical to a hop female plant before flower bud differentiation f.

(15) The method of (13) or (14) above, wherein the chemical application is a foliar application or foliar spray.

(16) A method of producing a hop plant variety comprising the following steps of:
1) forming a fertile male flower capable of forming pollen on a hop female plant;
2) crossbreeding with the male flower and a female flower; and
3) screening for a progeny produced by the crossbreeding.

According to the method for physiologically controlling the sexuality of hop which becomes possible by the present invention, the crossbreeding between female plants and the self-fertilization of a female plant, which have not been much practiced up to date, become possible. Further, the breeding and genetic analysis using progenies obtained from such a crossbreeding also become possible.

The present specification encompasses the contents described in the specification and/or drawings of Japanese Patent Application No. 2011-179873 from which the present application claims priority.

BRIEF DESCRIPTION OF DRAWINGS

The patent or application file contains at least one drawing executed in color. Copies of this patent or patent application publication with color drawing(s) will be provided by the Office upon request and payment of the necessary fee.

In FIG. 1, "1" to "6" show the initial stage of a male flower formed on each variety, and "7" shows the flowering stage. The varieties are: "1", "Kirin No. 2"; "2", "Kaikogane"; "3", "Kitamidori"; "4", "Toyomidori"; "5", "HALLERTAUER MITTELFUH"; "6", "HERSBRUCKER"; and "7", "Kirin No. 2".

FIG. 6 shows the female flowers and male flowers, which were formed on "Kirin No. 2" by applying different chemicals. The chemicals and the application concentration thereof are: "1", STS 4 mM; "2", silver nitrate 8 mM; "3", AVG 0.2 mM; and "4", AVG 0.5 mM.

FIG. 7 shows the RAPD analysis results of 10 progeny individuals obtained by crossbreeding the pollen of a male flower formed on the variety "Kirin No. 2" with the "Kirin No. 2". Electrophoresis images of the amplified products by A: Primer 1 (5'-GTCGCCGTCA-3' (SEQ ID NO: 1)), B: Primer 2 (5'-ACTTCGCCAC-3' (SEQ ID NO: 2)), C: Primer 3 (5'-AAGCCTCGTC-3' (SEQ ID NO: 3)), and D: Primer 4 (5'-CATCCCCCTG-3' (SEQ ID NO: 4)). M: Molecular weight marker (EcoRI- and HindIII-digested products of XDNA), K2: "Kirin No. 2", 1-10: Progenies.

MODES FOR CARRYING OUT THE INVENTION

Figure 1:
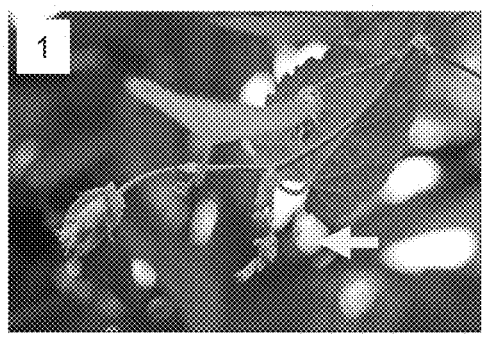
FIG. 1 shows a male flower (arrow) formed on a female plant.
Figure 1:
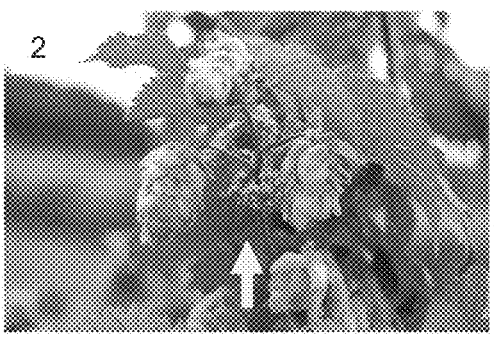
Figure 1:
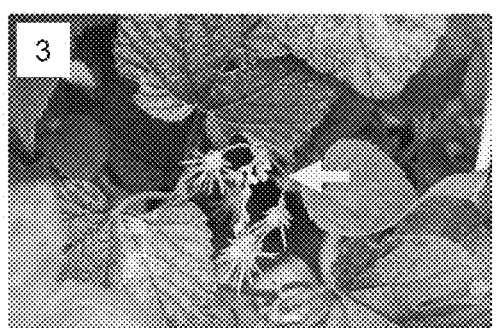
Figure 1:
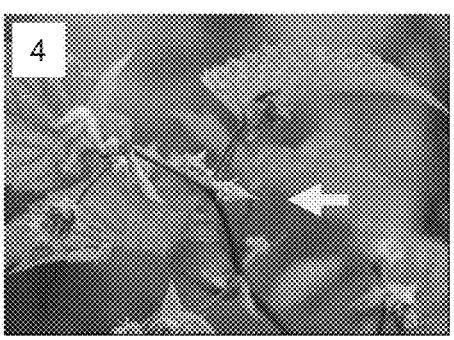
Figure 1:
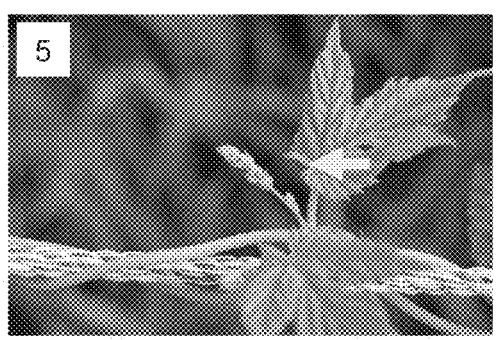
Figure 1:
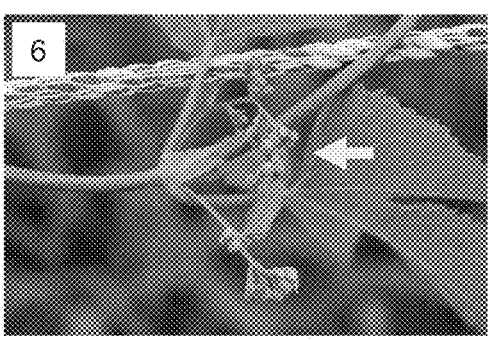
Figure 1:

Hereinafter, the present invention will be described more in detail.

<Cultivation of Hop>

The cultivation of hop may be carried out by the method generally practiced. For example, "Hoppu tashuusaibai no shingijutsu (in Japanese) (New technology for hop high producing cultivation), by Tsunenari Hamaguchi, Rural Culture Association Japan" describes in detail the cultivation method for the production purpose. However, hop may be cultivated by any method as long as the method employs the conditions for forming a male flower on a female plant in order to carry out the present invention. For example, hop can also be cultivated in a greenhouse instead of a farm site. An example of the greenhouse cultivation is described below, but the cultivation method to carry out the present invention is not limited thereto.

Suitable compost, e.g., Best Compost (Honen Agri), is put in pots having an inner diameter of about 20 to 40 cm, a plant (preferably an over-wintering plant) is planted and a suitable fertilizer is applied. For example, Magamp-K (Hyponex Japan, Japan) is added and used in an appropriate amount to the culture soil as a base manure, and may be applied thereafter in an appropriate amount once in 2 months. Hop is a vine plant, and it is hence desirable to provide supports around which the vines twine. Racks are used in the business cultivation, but supporting strus, suspended ropes, or the like, may be used as the supports in the greenhouse cultivation. To increase the number of the induced male flowers, an effective way is to cut a primary lateral branch leaving 3 nodes intact to promote the development of a secondary lateral branch. To prevent damages caused by insects such as spider mites, or the like, and damages caused by diseases such as downy mildew, or the like, it is desirable to practice a suitable pest control management against pests such as chemical spray, or the like. Flop is a short-day flowering plant. The degree of vegetative growth (the number of nodes) and the day length are important factors in forming the induced male flower, and the conditions vary depending on hop varieties (Thomas, G. G. and Shewabe, W. W. Ann Bot (1969) 33: 781-793). Generally, when a variety cultivated in Japan is planted in spring, it blooms in summer time under the natural day length.

<Treatment for Controlling the Sexuality>

The present invention provides a method for controlling the sexuality of hop, comprising applying a chemical to a hop female plant once or more and thereby forming a fertile male flower capable of producing pollen on the female plant, wherein the chemical reduces a reaction with endogenous ethylene in the female plant.

The present invention further provides a method for producing a hop plant variety, comprising a step of forming a fertile male flower capable of producing pollen on the female plant.

In order to form a hop male flower on a female hop plant, a treatment for reducing a reaction with endogenous ethylene in the female hop plant is applied. The treatment is preferably carried out before flower bud differentiation. Specifically, any of ethylene biosynthesis inhibitors, ethylene action inhibitors, or ethylene adsorbents, or a combination thereof, is applied to a female hop plant. The term "forming a male flower on a female plant" as used herein indicates that the male flower is induced on a female plant and deveolps thereon.

Examples of the ethylene biosynthesis inhibitors include, but not limited thereto, aminooxyacetic acid, 2-aminoisobutylic acid, amino ethoxy vinyl glycine (AVG), cobalt chloride, rhizobitoxine, and the like.

Examples of the ethylene action inhibitors include, but not limited thereto, silver thiosulfate complex (STS), 1-methylcyclopropene, silver nitrate, and the like.

Examples of the ethylene adsorbents include, but not limited thereto, activated carbon, zeolite, and the like.

The application may be carried out by any method as long as the reaction with endogenous ethylene in the female hop plant can be reduced. In such a case, for example, the above chemicals, or the like, may be sprayed on or applied to the plant body or the surrounding soil in a concentration at which the endogenous ethylene level can be reduced, or a concentration at which the reaction with endogenous ethylene can be inhibited. Preferably, the above-mentioned chemicals may be applied to or sprayed on a part of or entirely throughout a leaf area (preferably, the surface of a leaf) of the plant body, and the number of leaves to be treated may be one or more leaves, preferably a plurality of leaves, and the application or spraying may be carried out onto all the leaves. Such a foliar application or foliar spray is more advantageous and effective than dropping onto a growing shoot tip. The dropping onto a growing shoot tip is most likely to stop the growth of buds and causes to require a long time for making a hop male flower. When the flowering of the male flower is later than the female flowering time, the subsequent crossbreeding becomes difficult. For this reason, the foliar application or foliar spray which does not cause the stop of growth is more practical and easier to practice than the dropping onto a growing shoot tip.

The concentration of the chemical to be applied varies depending on the type of chemical and hence a suitable concentration has to be preferably selected and used. For example, when STS is used as the chemical, the application concentration is, but is not limited to, 0.1 to 100 mM, preferably 0.4 to 50 mM, more preferably 1 to 20 mM, relative to the silver ion concentration. When the concentration is below 0.1 mM, the male flower inducing effect is not expected and hence is not desirable, and when the concentration exceeds 100 mM, the growth is inhibited and hence is not desirable. Because it is considered that the chemical concentration at which a plant is tolerant to withering varies depending on the vegetative growth vigor, it is desirable to select a treatment concentration in accordance with the conditions of a plant to be treated.

The chemical is typically applied in the liquid forms such as solutions, suspensions, emulsions, or the like, but optionally, may be in the solid forms such as powders, wettable powders, granules, or the like, or optionally a solid form may be reconstituted into a liquid form before use.

Examples of the solvent in which the chemical is dissolved or suspended include, but not limited thereto, water, alcohols (e.g., methanol, ethanol, and the like), dimethyl sulfoxide (DMSO), dimethylformamide (DMF), ethylene glycol, acetonitrile, acetone, acids, alkalines, and the like.

To enhance emulsifiability or dispersibility to water, an agriculturally acceptable surfactant or dispersing agent may be mixed. Examples of the surfactant include polyoxyalkylene higher alkyl ether sulfuric acid ester salt, fatty acid alkyl ester salt, dialkyl phthalate salt, phosphate ester, alcohol ethoxylate, ethoxylated castor oil, higher alcohol alkylene oxide adduct, and the like. Examples of the dispersing agent include carboxymethylcellulose, polyoxyalkylene hydrogenated castor oil sulfuric acid ester salt, alkyl naphthalenesulfonate, alkyl aryl ether sulfate, alkyl polyglucoside, and the like.

Further, the liquid formulation may further contain other additives such as agriculturally acceptable stabilizers, binders, spreaders, penetrants, antifoaming agents, coloring agents, antifreezing agents, and the like.

The application of a chemical is carried out once or more before flower bud differentiation. Since flower buds are differentiated sequentially, the application is desirably carried out several times when many male flowers need to be formed. Also, considering that the period from the chemical treatment to the blooming is important for the efficiency of forming male flowers, the application is desirably carried out several times because the probability of the treatment within proper period increases. When the application is carried out several times, preferably the chemical is applied at week intervals, such as about 2 week intervals.

<Crossbreeding and Seed Production>

Since the hop female flower does not have any stamen, the plant emasculation, or the removal of stamens, is not needed, and thus the intended crossbreeding can be achieved by adhering the pollen of a male flower to the stigma of a female flower of the same plant or another female plant. However, since hop is an anemophilous plant, it is necessary to eliminate as much as possible the possibility of pollination by unintended pollen in order to obtain seeds through the crossbreeding of interest. To achieve it, it is effective to block the unintended pollination by bagging, or the like, after the artificial pollination is carried out. Where an unintended pollination may occur, the bagging before the pollination is also effective. Two to 3 months later from the pollination, full grown cones are harvested to obtain the seeds. Accordingly, the present invention also provides a method for obtaining seeds from the cone obtained by producing a female plant with male flowers formed thereon by using the method for controlling the hop sexuality as described above and then crossbreeding the pollen of the female plant with the female flower of the female plant or a female flower of another female plant.

Because it is generally difficult to germinate a hop seed, a low temperature treatment is needed. It is documented that the germination rate without low temperature treatment is less than 5% (MUROGA Toshimasa and ITO Tadahisa, Studies on the germination of seeds in hop. I.: Effect of low temperature and alternating temperature on germination, Japanese Society of Breeding (Japan), Abstracts of the 4th Annual Meeting, p. 48, 1953). The enhanced germination rate can be anticipated by carrying out low temperature treatment at 2 to 3° C. for about 2 months (Haunold, A and Zimmermann, C. E. Crop Science (1974) 14:774-776).

The present invention further provides a method for obtaining hop plants from the seeds obtained by the above-mentioned method. Specifically, the seeds are germinated and may be cultivated by the technique described in the above <Cultivation of hop>, or the use of sterile culture is also effective to enhance the efficiency for obtaining a plant from the crossbred seeds. After an embryo is formed, the ovule or seed is aseptically taken out from the surface-sterilized ovary and incubated in a common plant growth medium such as Murashige—Skoog (MS) medium containing a sugar source such as sucrose, glucose, fructose, or the like, thereby obtaining a plant. Alternatively, an embryo may be aseptically taken out from the ovule or seed and incubated. Where the seed coat is hardened to the extent that it tolerates the sterilization, the surface of seed may be sterilized and incubated without further treatment or incubated after removing the seed coat. Further, the endosperm is removed and only the embryo may be incubated. However, as the embryo develops, the efficiency for obtaining a plant by the incubation becomes higher. It is thus desirable to avoid unnecessarily incubating an undeveloped embryo but carry out the incubation using a sufficiently developed embryo, or the like, unless the infertility is particularly predicted.

The addition of a plant hormone, or the like, to the medium is not fundamentally required, and medium commonly used for incubating a plant, such as Murashige—Skoog medium containing 3% sucrose or 2% glucose may be used. Since Murashige—Skoog medium has a comparative high salt concentration, good growth may sometimes be achieved depending on the variety by adjusting the concentration of magnesium sulfate, potassium dihydrogen phosphate, ammonium nitrate, potassium nitrate or calcium chloride to one half or one quarter. In incubating an immature embryo, the addition of gibberellin, low concentration (less than 1 ppm) of auxin, casein, coconut milk or a yeast extract may sometimes contribute to the effective obtention of a plant. Also, in incubating an immature embryo, it is generally recommended to increase the concentration of sugar sources.

Such incubation enables to obtain a plant from the seed, which was once difficult to germinate due to causes such as dormancy, embryo immaturity, endosperm immaturity, or the like. For these tissue incubations or cultures, such techniques are described in In-vitro culture of horticultural plants, 1988, p. 280-290, Shibata Hario Glass Co., Ltd. (Japan), Plant Tissue Culture Atlas, 1987, p. 252-265, R & D Planning Inc. (Japan), or the like.

<Breeding>

The breeding procedures using the present invention remain unchanged from the conventional methods, except that the treatment for forming a male flower is carried out. Specifically, there are no procedures different from the conventional methods in terms of cultivation, crossbreeding, seed production, progeny breeding, propagation or multiplication (which may be achieved by dividing or cutting, for example), evaluation, and selection, and the works practiced by those breeding hop may be carried out.

The breeding according to the present invention can crossbreed female plants with each other and so it is possible to obtain progenies directly utilizing the parents whose cone traits are already evaluated. Further, a progeny by the self-fertilization of any female plant can also be obtained. The crossbred progeny, which is enabled to obtain by the present invention, is further bred by the conventional breeding method.

When the present invention is utilized, the breeding using the parents whose cone traits and productivity are confirmed becomes possible, thereby making it easy to accumulate traits desired for the cone traits and productivity. The present invention is effective to breed a variety, but not limited thereto, for example a variety having a combination of the traits from both the parents each having a characteristic flavor component, a variety having a high content of a acid with a high probability from the parents each having a high a acid content, a variety having a high a acid content and a characteristic flavor component from the parents, one of which has a high a acid content and the other has a characteristic flavor component, or the like.

The present invention further contributes to enhance the efficient breeding of varieties having many useful traits without limiting to the cone traits. Unlike the male plants, in the varieties utilized for cone production in practice, various traits such as cultivation properties, resistance to diseases, environmental adaptability, and the like, in addition to the cone traits and cone productivity, are grasped in cone producing districts. When using such varieties as parents, a variety having a combination of useful traits or a variety complementing unnecessary traits of the parents can be bred more directly.

<Cone>

The present invention further provides a cone of a novel plant produced from the embryo or seed obtained by the above-mentioned method of the present invention. The novel plant obtained by crossbreeding has new cone qualities different from those of the parents, as described in the above Background Art. A fertile male flower capable of forming pollen is formed on a female plant by the above-mentioned method, and subsequently the female plants are crossbred with each other to obtain a novel plant and cones thereof.

<Method of Screening for Hop Plant>

The present invention further provides a method of screening for a hop plant, comprising breeding hop plans from different embryos or seeds of claim 8, determining, as a genetic marker, a DNA polymorphism linking to a trait characteristic of each hop plant, making a genetic linkage map between the genetic marker and the trait, and screening for a hop plant of interest from the hop plants using the genetic linkage map.

As described above, the utilization of the present invention enables to obtain a progeny between female plants and a progeny of the female plant self-fertilization. The traits of these progenies are examined, and the genetic analysis was carried out for the segregated traits. The genetic analysis employs routinely used techniques, a hereditary pattern is presumed, and genetic linkages among traits are calculated. The traits used herein include DNA polymorphisms. A specific DNA polymorphism linked to a specific trait can be used as a genetic marker. Examples of the method for detecting such a DNA polymorphism include well known RAPD (Random Amplified Polymorphic DNA), SSR (Simple Sequence Repeats), ISSR (Inter-Simple Sequence Repeat), AFLP (Amplified Fragment Length Polymorphism), RFLP (Restriction Fragment Length Polymorphism), and the like. In Example 7 to be described later, the RAPD method is illustrated, which comprises the detection of DNA polymorphism wherein genomic DNA used as a template is amplified by PCR in the presence of primers (typically, random primers) and the difference in the amplified fragment size, or the like, of the genomic DNA is detected by electrophoresis, or the like.

The genetic linkage map between traits is constructed from the calculated genetic linkage distances. Further, for quantitative traits, a genetic marker can be found by the QTL analysis using the genetic linkage map of DNA polymorphisms.

By detecting the thus obtained genetic marker, the intended plant having the target trait can be screened for. Specifically, DNA is extracted from a part of plant body, or the embryo or seed, the genetic marker is amplified by a gene amplification method such as the PCR method which uses primers to detect the genetic marker, and the presence or level of the marker can be measured by a routine method (e.g., fluorescent labeling or electrophoresis). The obtained plant can be evaluated for selection or elimination based on the measured presence or level of the marker.

The progenies between female plants are theoretically all female plants, and the traits and productivity of cone can be evaluated. Since the conventional crossbreeding between a female plant and a male plant produces more than a few male plants, all the progenies could not be evaluated for the traits and productivity of cone. According to the present invention, the cone traits and productivity of all the progenies can be evaluated and so the precision of genetic analysis concerning the cone traits and productivity is improved.

<Method for Specifying a Chromosomal Region in which Hop Gene is Present>

The present invention further provides a method for specifying a chromosomal region on which a hop gene is present using the genetic linkage map constructed by the above method.

When the genetic linkage map constructed by utilizing the present invention is used, the chromosomal region on which the target gene is present can be specified. More specifically, when the genetic markers linking to both sides of the target trait are detected on a chromosome, the intended gene is revealed to be present in the region sandwiched between these genetic markers. When a clone is specified from the cloned hop DNAs using as an indicator a genetic marker linking to the target trait, it becomes possible to specify the clone having the DNA which lies near the intended gene. The stronger the linkage between the genetic marker and the intended trait, the nearer the clones to the target gene can be identified. It is revealed that the target gene is either one of the genes present within the region sandwiched between the clones found on both sides of the target trait.

EXAMPLES

Hereinafter, the present invention is described more specifically with reference to Examples. However, the scope of the present invention is not limited to these Examples.

Example 1

Forming a Male Flower on a Female Plant Bred at a Farm Site (Part 1)

Hop varieties (female plants) "Kirin No. 2", "Kaikogane" (Japan variety registration No. 20), "Kitamidori" (Japan variety registration No. 1978), "Toyomidori" (Japan variety registration No. 160), "HALLERTAUER MITTELFUH" and "HERSBRUCKER", each of which is an over-wintering plant or strain, were planted at a farm site located in Sakura city, Tochigi (Japan), on Mar. 18 or 19, 2010 and cultivated in accordance with a routine method. Upon cultivation, ropes were horizontally stretched, instead of installing racks, at a height of about 1 m 50 cm above the ground to use as supports for the vines. The primary lateral branch, when elongated was cut leaving 3 nodes intact to promote the development of the secondary lateral branch. The above hop varieties are available from public institutions and cooperatives associated with the above varieties, such as National Clonal Germplasm Repository—Corvallis (NCGR-Corvallis, Oreg., USA).

CHRYSAL K-20C (Chrysal Japan Limited, Osaka, Japan), a commercial silver thiosulfate (STS) solution, was diluted with distilled water so as to give silver ion concentrations of 2 mM and 20 mM. These solutions were applied to the surface of all the leaves, which were not withered, using a paint brush 3 times every 2 weeks starting on Jun. 29, 2010. Also, distilled water was applied as a control area. In the 2 mM area, the applied leaves were partially browned but the remaining part continued growing. In the 20 mM area, the applied leaves were withered and the growth thereafter was inhibited.

Figure 2:
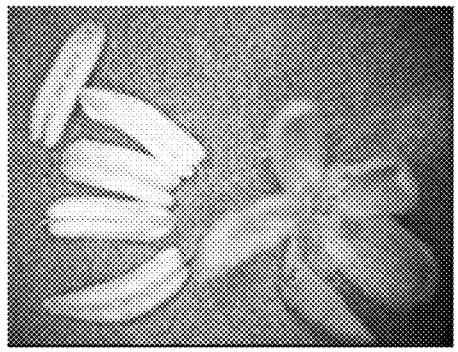
FIG. 2 shows a division image of the male flower formed on the variety "Kirin No. 2". It has 5 perianths and 5 anthers as in typical male flowers.
Figure 3:
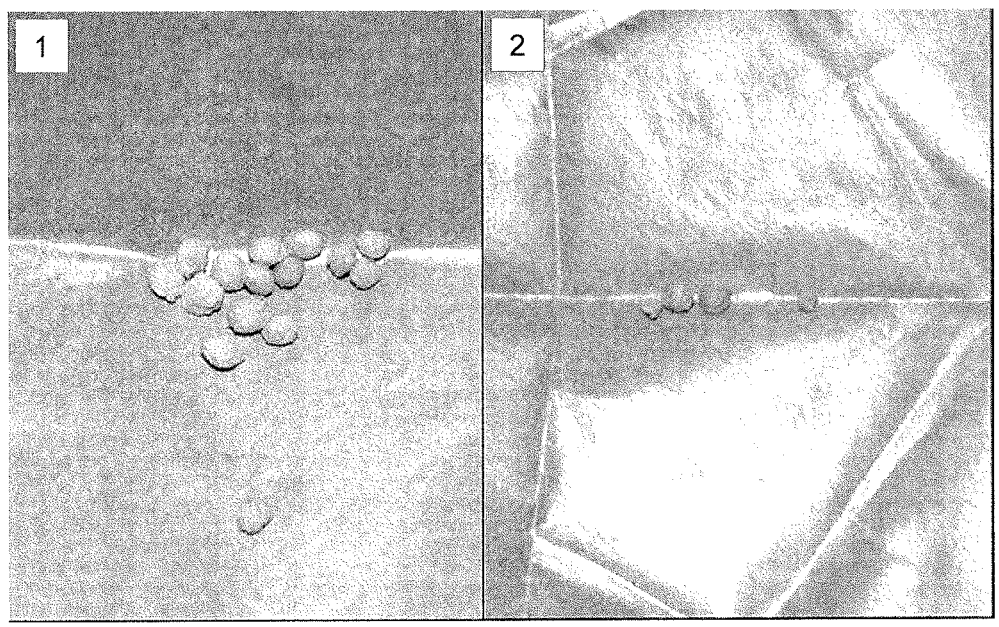
FIG. 3 shows the seeds obtained through crossbreeding the pollen of a male flower formed on the variety "Kirin No. 2". The crossbreeds are; "1", "Kirin No. 2" (♀)×"Kirin No. 2" (♂); and "2", "HALLERTAUER MITTELFUH" (♀)× "Kirin No. 2" (♂).

In all of the 6 varieties tested, formation of only a female flower was observed in the control areas, while formation of a male flower was observed in the 2 mM area (FIG. 1). The morphology of the male flowers formed on the above hop varieties (female plants) had 5 perianths and 5 anthers (FIG. 2), as in the male flower on a male plant, the pollen production was confirmed. The mature pollen of "Kirin No. 2" was dyed with acetocarmine (FIG. 3-1). Further, when the pollen was scattered on 1% agar containing 10% sucrose and allowed to stand at room temperature for 5.5 hours, the elongation of a pollen tub was observed (FIG. 3-2).

As described above, the application of the STS solution enabled to make a male flower, which has the normal morphology and is capable of producing pollen, on a female plant.

Example 2

Forming a Male Flower on a Female Plant bred in a Greenhouse (Part 1)

An over-wintering plant or strain of the hop variety "Kirin No. 2" was planted in pots charged with Best culture soil (Honen Agri, Japan) having an inner diameter of about 25 cm. Magamp-K (Hyponex Japan, Japan) was added in an appropriate amount to the culture soil as base manure, and Magamp-K was additionally applied thereafter in an appropriate amount about once in 2 months. Ropes were suspended down from the beam of a greenhouse and used as supports for the vines. The greenhouse had the lowest temperature of 15° C. Agricultural chemicals were sprayed as necessary for pest control.

CHRYSAL K-20C (Chrysal Japan Limited, Osaka, Japan), a commercial silver thiosulfate (STS) solution, was diluted with distilled water so as to give silver ion concentrations of 0.1 mM, 0.2 mM, 0.4 mM, 2 mM and 20 mM. These solutions were applied to the surface of all the leaves, which were not withered, using a paint brush 3 times every 2 weeks from the time at which the plant grew to 12-15 nodes. Also, distilled water was applied as a control area. Thereafter, the main stem was cut at about the 17th node to avoid that the plant reached the ceiling of the greenhouse. The application to the surface of the leaves was carried out in the same manner as above at the time of the primary lateral branch having grown to the 3rd node. The primary lateral branch, when further elongated, was cut leaving 3 nodes intact to promote the development of the secondary lateral branch. In the 2 mM area, the applied leaves were partially browned but the remaining part continued growing. In the 20 mM area, the applied leaves were withered and the growth thereafter was inhibited.

Only female flowers were observed in the control area, 0.1 mM area, 0.2 mM area and 0.4 mM area, whileas male flowers were observed in the 2 mM area.

Example 3

Forming a Male Flower on a Female Plant Bred in a Greenhouse (Part 2)

An over-wintering plant of the hop variety "Toyomidori" was used and bred in the same manner as in Example 2.

CHRYSAL K-20C (Chrysal Japan Limited, Osaka, Japan), a commercial silver thiosulfate (STS) solution, was diluted with distilled water so as to give a silver ion concentration of 2 mM. The solution was applied to the surface of all the leaves, which were not withered, using a paint brush twice every 2 weeks from the time at which the plant grew to 12-15 nodes. Also, distilled water was applied as a control area. Thereafter, the main stem was cut at about the 17th node to avoid that the plant reached the ceiling of the greenhouse. The primary lateral branch, when further elongated, was cut leaving 3 nodes intact to promote the development of the secondary lateral branch. In the 2 mM area, the applied leaves were partially browned but the remaining part continued growing.

Only female flowers were observed in the control area, while male flowers were observed in the treated area.

Example 4

Crossbreeding and Seed Production

A male flower bunch of "Kirin No. 2" formed in Example 1 was cut and put in an Erlenmeyer flask, and stored in a desiccator in a low temperature warehouse (at 4° C.). The stored male flower bunch was taken out when the female flowers flowered, and the pollen was adhered to the stigma of female flowers of "Kirin No. 2" and "HALLERTAUER MITTELFUH", respectively for the crossbreeding. The crossbred inflorescences were bagged in consideration of avoiding the fertilization caused by pollen which is not desired. The cones were harvested about 2 months later from the crossbreeding and disassembled to obtain ripe seeds. About 300 seeds were obtained from about 100 cones of the self-fertilized "Kirin No. 2", and 10 seeds were obtained from about 10 cones in the crossbreeding with "HALLERTAUER MITTELFUH".

Example 5

Forming a Male Flower on a Female Plant Bred at a Farm Site (Part 2)

An over-wintering plant or strain of the hop variety (female plant) "Kirin No. 2" was cultivated at a farm site located in Sakura city, Tochigi, Japan, in 2012, in the same manner as in Example 1. CHRYSAL K-20C, a commercial silver thiosulfate (STS) solution, was diluted with distilled water so as to give a silver ion concentration of 2 mM. The solution was sprayed onto the entire body using a sprayer 3 times every week starting on May 24, 2012. The application to the leaves was carried out as the control in the same manner as in Example 1. As in the application to the leaves, the male flowers were observed also in the spraying onto the entire body from the end of June. As the control areas, an area to which distilled water was applied and an area on which distilled water was sprayed were arranged, but both of them had female flowers only.

Also, an over-wintering plant or strain of the hop variety (female plant) "Kirin No. 2" was cultivated at a farm site located in Ohshu city, Iwate, Japan, in 2012, in accordance with a routine method. CHRYSAL K-20C, a commercial silver thiosulfate (STS) solution, was diluted with distilled water so as to give silver ion concentrations of 2 mM and 20 mM. These solutions were sprayed onto the entire body using a sprayer 3 times every week starting on Jun. 6, 2012. The application to the leaves was carried out as the control in the same manner as in Example 1. The plant body and leaves continued growing without withering in both treatments even in the 20 mM area. As in the application to the leaves, the male flowers were observed also in the spraying onto the entire body from the mid-July. In the 2 mM area, however, the male flower had a fewer frequency and almost all were female flowers. In contrast, the male flowers were efficiently formed in the 20 mM area. As the control areas, an area to which distilled water was applied and an area on which distilled water was sprayed were arranged, but both of them had female flowers only. Additionally, the plant used in the test was cultivated by the method used for producing hop and had a vigorous growth.

Example 6

Forming a Male Flower Formed on a Female Plant Bred in a Greenhouse (Part 3)

An over-wintering plant or strain of the hop variety "Kirin No. 2" was cultivated in the same manner as in Example 2.

CHRYSAL K-20C, an ethylene action inhibitor, in silver ion concentrations of 2 mM, 8 mM and 16 mM; silver thiosulfate (STS) in silver ion concentrations of 4 mM, 8 mM, and 16 mM; a solution of silver nitrate in concentrations of 8 mM, 16 mM, and 32 mM; and an amino ethoxy vinyl glycine (AVG) solution, an ethylene synthesis inhibitor, in concentrations of 0.2 mM, 0.5 mM and 1 mM, were respectively applied to the surface of all leaves, which were not withered, using a paint brush in the same manner as in Example 2 4 times in total about every 10 days from the time at which the plant grew to 12-15 nodes (May 25, 2012). Silver thiosulfate (STS) was prepared by mixing sodium thiosulfate pentahydrate and silver nitrate in a molar ratio of 8:1. An area to which water was applied was arranged as a control area.

Figure 4:
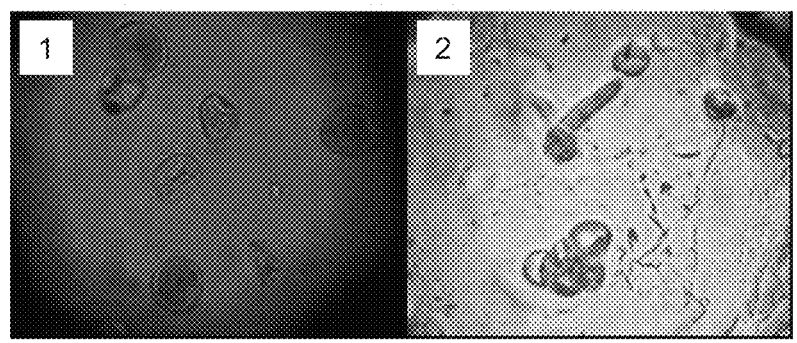
FIG. 4 shows: "1", the pollen dyed with acetocarmine of a male flower formed on "Kirin No. 2"; and "2", the state of a germinated pollen tube (i.e., an elongated pollen tube) on 1% agar (containing 10% sucrose).
Figure 5:
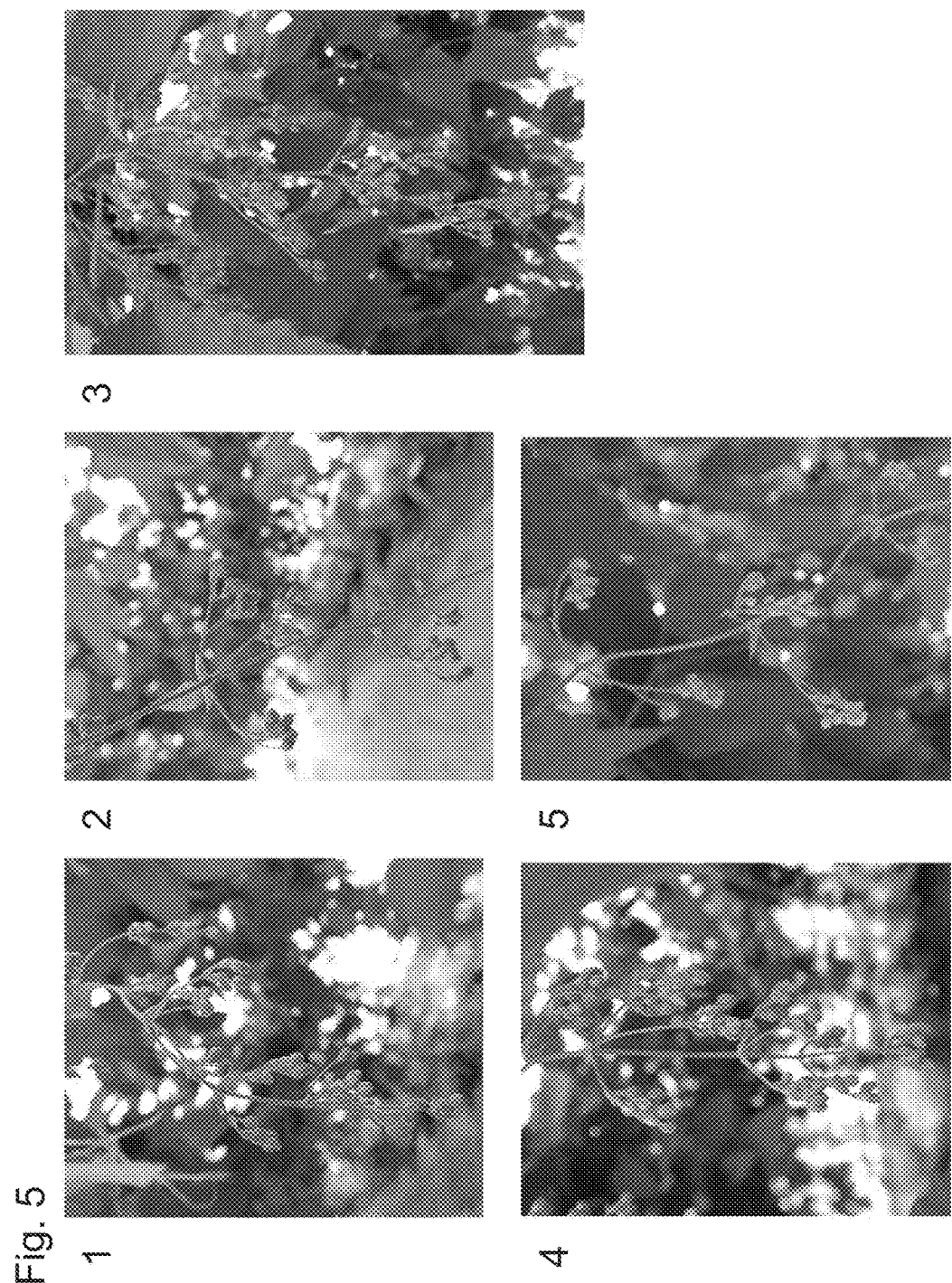
FIG. 5 shows male flowers formed on "Kirin No. 2" by applying different chemicals. The chemicals and the application concentration thereof are: "1", STS 8 mM; "2", STS 16 mM; "3", silver nitrate 16 mM; "4", silver nitrate 32 mM; and "5", AVG 1 mM.

In all of the areas to which CHRYSAL K-20C, STS and silver nitrate were applied, the applied leaves were partially browned but continued growing. In the AVG treated area, the applied leaves suffered from chlorosis but continued growing. Flower buds were observed from the beginning of July and the sexuality was determined from the mid-July. Only female flowers were observed in the control areas. The male flowers were observed in the CHRYSAL K-20C 2 mM area, 8 mM area and 16 mM area; the STS 8 mM area (FIG. 5-1), 16 mM area (FIG. 5-2); the silver nitrate 16 mM area (FIG. 5-3), 32 mM area (FIG. 5-4); and the AVG 1 mM area (FIG. 5-5). In the STS 4 mM area (FIG. 6-1); the silver nitrate 8 mM area (FIG. 6-2); the AVG 0.2 mM area (FIG. 6-3); and the AVG 0.5 mM area (FIG. 6-4), the female flowers were predominantly observed but the male flowers were observed in part.

As described above, not only CHRYSAL K-20C, a commercial ethylene action inhibitor, but also the applications of STS and silver nitrate, which are ethylene action inhibitors, and AVG, which is an ethylene synthesis inhibitor, enabled to induce the male flower. Further, the plant grew without withering and the male flowers were observed even when CHRYSAL K-20C was applied in a higher concentration than the concentrations which were effective in the earlier Examples. In the present test, the plants used had a vigorous vegetative growth and required a longer time from the chemical treatment to the flowering than the tests conducted so far. When the plant used had a vigorous growth, it was verified that the plant does not wither by the chemical treatment even in a higher concentration and that male flowers were formed on the plant. Furthermore, in the CHRYSAL K-20C 2 mM area and 8 mM area of the present Examples, flower bunches of only male flowers and flower bunches of male flowers with female flowers partially thereon were observed. The flower bunches of female flowers mixed with male flowers were not found in the CHRYSAL K-20C 16 mM area.

Example 7

DNA Analysis of Progenies

The self-fertilized seeds of "Kirin No. 2" obtained in Example 4 were stored in a refrigerator for more than 6 months. Subsequently, the seed coat was removed from the surface-sterilized seed and incubated in Murashige and Skoog (MS) medium containing 3% sucrose. The culture conditions were 25° C. and 16 hr day-length. DNA was extracted from the leaf of the obtained aseptic plant using a DNeasy Plant Mini Kit (Qiagen) in accordance with the instructions attached thereto. Using the DNAs of "Kirin No. 2" and 10 progenies thereof, DNA polymorphisms were compared by the RAPD method. For the RAPD method, the following 4 random primers were used. Primer 1: 5'-GTCGCCGTCA-3' (SEQ ID NO: 1), Primer 2: 5'-ACTTCGCCAC-3' (SEQ ID NO: 2), Primer 3: 5'-AAGCCTCGTC-3' (SEQ ID NO: 3), Primer 4: 5'-CATCCCCTG-3' (SEQ ID NO: 4). Further, PCR (Polymerase Chain Reaction) was carried out using a TaKaRa Ex Taq (TAKARA BIO INC.) under the following program.
95° C., 5 minutes→(95° C., 1 minute→34° C., 1 minute→72° C., 1 minute)×45 cycles→72° C., 5 minutes. The PCR amplified product was separated by 1% agarose gel using TAE buffer and visualized with ultraviolet radiation at 302 nm.

As shown in FIG. 7, the progenies had polymorphisms different from that of "Kirin No. 2". It revealed that the progenies are not identical with "Kirin No. 2". The polymorphisms were also observed in the progenies and the genetic segregation was verified. The linkage between the bands can be evaluated by writing down the presence or absence of each band showing polymorphisms in those progenies.

The bands obtained by the RAPD method employed this time are inherited by the progeny as dominant traits. Theoretically, when 2 bands, which are segregated in self-fertilization progenies, are independently inherited, the individuals with both bands, individuals with only Band 1, individuals with only Band 2, or individuals without band, are segregated in a ratio of 9:3:3:1. Additionally, when each band is completely linked in the coupling configuration, the individuals with both bands or individuals without band are segregated in a ratio of 3:1. When each band is completely linked in the repulsion configuration, the individuals with both bands, individuals with only Band 1, and individuals with only Band 2 are segregated in a ratio of 2:1:1. As described above, when both bands are in the relationship of the coupling configuration and completely linked, the individuals with both bands and individuals without band are segregated in a ratio of 3:1, and no individuals with either one of the bands appear. When a dominant marker is evaluated in the coupling configuration, the recombination value, i.e. the degree of linkage, can be calculated by the appearance frequency of an individual having only one of the bands.

For example, the presence of Band 1 detected by Primer 1 and Band 2 detected by Primer 2 completely matches in each of 10 individuals, and no recombination was found. Consequently, it is considered that these 2 bands are strongly linked. Also, the presence of Band 3 detected by Primer 3 and Band 4 detected by Primer 4 matches in nine of 10 individuals, i.e., except 1 individual (Progeny 9). Without considering the possibility of double recombination, the simple calculation with no statistical treatment projects that these bands are linked with a recombination value of 10% (FIG. 7, Table 1). The reliable genetic distance calculation requires an increased number of the progeny, but the linkage can be analyzed as described above since plural polymorphisms are observed among the progenies. Thus, it is evident that, in the progenies produced by the induced male flowers, a genetic marker can be obtained and a genetic linkage map can be prepared by combining plural linked traits.

TABLE 1

Presence of amplified bands by RAPD in Kirin No. 2 self-fertilization progenies

| | Kirin No. 2 | Progeny | | | | | | | | | |
|---|---|---|---|---|---|---|---|---|---|---|---|
| | | 1 | 2 | 3 | 4 | 5 | 6 | 7 | 8 | 9 | 10 |
| Band 1 | + | + | + | + | − | + | + | − | + | − | − |
| Band 2 | + | + | + | + | − | + | + | − | + | − | − |
| Band 3 | + | − | + | − | + | − | − | + | + | + | + |
| Band 4 | + | − | + | − | + | − | − | + | + | − | + |

+: Band, present
−: Band, absent

INDUSTRIAL APPLICABILITY

The present invention is applicable for breeding hop, developing good quality cones, and the like, and hence is useful.

Sequence Listing Free Text
 SEQ ID NOs. 1 to 4: Primers
 All publications, patents and patent applications cited herein are incorporated herein by reference in their entirety.

The invention claimed is:

1. A method of producing a hop plant variety comprising the following steps of:
   1) forming a fertile male flower capable of producing pollen on a hop female plant;
   2) crossbreeding with the male flower and a female flower; and
   3) screening for a progeny produced by the crossbreeding, wherein step 1) comprises applying a chemical to a hop female plant once or more, to thereby form a fertile male flower capable of producing pollen on the female plant,
   and wherein said chemical is an ethylene biosynthesis inhibitor, an ethylene action inhibitor, or a combination thereof.

2. The method of claim 1, wherein the ethylene biosynthesis inhibitor is selected from the group consisting of aminooxyacetic acid, 2-aminoisobutylic acid, amino ethoxy vinyl glycine (AVG), cobalt chloride, and rhizobitoxine.

3. The method of claim 1, wherein the ethylene action inhibitor is selected from the group consisting of silver thiosulfate complex (STS), 1-methylcyclopropene, and silver nitrate.

4. The method of claim 1, comprising applying the chemical to a hop female plant before flower bud differentiation.

5. The method of claim 1, wherein the chemical application is a foliar application or foliar spray.

* * * * *

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: primer

<400> SEQUENCE: 1
gtcgccgtca                                                         10

<210> SEQ ID NO 2
<211> LENGTH: 10
```

```
<212> TYPE: DNA
<213> ORGANISM: Artificial Sequence
<220> FEATURE:
<223> OTHER INFORMATION: primer

<400> SEQUENCE: 2
acttcgccac                                                          10

<210> SEQ ID NO 3
<211> LENGTH: 10
<212> TYPE: DNA
<213> ORGANISM: Artificial Sequence
<220> FEATURE:
<223> OTHER INFORMATION: primer

<400> SEQUENCE: 3
aagcctcgtc                                                          10

<210> SEQ ID NO 4
<211> LENGTH: 10
<212> TYPE: DNA
<213> ORGANISM: Artificial Sequence
<220> FEATURE:
<223> OTHER INFORMATION: primer

<400> SEQUENCE: 4
catccccctg                                                          10
```